(12) United States Patent
Argent et al.

(10) Patent No.: US 11,045,346 B2
(45) Date of Patent: Jun. 29, 2021

(54) OSTOMY APPLIANCE

(71) Applicant: SALTS HEALTHCARE LIMITED, Birmingham (GB)

(72) Inventors: Peter Argent, Birmingham (GB); Neil Wiltshire, Birmingham (GB)

(73) Assignee: Salts Healthcare Limited, Birmingham (GB)

( * ) Notice: Subject to any disclaimer, the term of this patent is extended or adjusted under 35 U.S.C. 154(b) by 718 days.

(21) Appl. No.: 14/765,219

(22) PCT Filed: Jan. 28, 2014

(86) PCT No.: PCT/GB2014/050212
§ 371 (c)(1),
(2) Date: Jul. 31, 2015

(87) PCT Pub. No.: WO2014/118518
PCT Pub. Date: Aug. 7, 2014

(65) Prior Publication Data
US 2015/0359657 A1    Dec. 17, 2015

(30) Foreign Application Priority Data

Feb. 1, 2013   (GB) .................................... 1301858

(51) Int. Cl.
*A61F 5/445* (2006.01)
*A61F 5/441* (2006.01)
*A61F 5/44* (2006.01)

(52) U.S. Cl.
CPC .............. *A61F 5/445* (2013.01); *A61F 5/441* (2013.01); *A61F 5/4405* (2013.01)

(58) Field of Classification Search
CPC combination set(s) only.
See application file for complete search history.

(56) References Cited

U.S. PATENT DOCUMENTS

| 3,570,490 | A  | * | 3/1971  | Berger ................... A61F 5/445 |
|           |    |   |         |                             604/332  |
| 4,219,023 | A  |   | 8/1980  | Galindo                              |
| 2002/0088080 | A1 | * | 7/2002  | Fenton .................... A61F 5/445 |
|           |    |   |         |                              15/389  |
| 2004/0089640 | A1 | * | 5/2004  | Bager ................. B29C 65/1645  |
|           |    |   |         |                           219/121.64  |
| 2005/0273065 | A1 | * | 12/2005 | Lillegaard ............. A61F 5/4405  |
|           |    |   |         |                              604/332  |
| 2006/0200101 | A1 | * | 9/2006  | Mullejans ............... A61F 5/445  |
|           |    |   |         |                              604/339  |

(Continued)

FOREIGN PATENT DOCUMENTS

WO        2011150936        12/2011

OTHER PUBLICATIONS

UK, Intellectual Property Office, Search Report dated May 28, 2013.

*Primary Examiner* — Guy K Townsend
(74) *Attorney, Agent, or Firm* — Morgan, Lewis & Bockius LLP

(57) ABSTRACT

An ostomy appliance having first and second walls connected to each other at or near their peripheries, the first wall having a stoma-receiving opening, and a waste collecting cavity defined between the first and second walls, wherein the second wall includes viewing portion through which the stoma-receiving opening can be viewed.

22 Claims, 4 Drawing Sheets

(56) References Cited

U.S. PATENT DOCUMENTS

| | | | | |
|---|---|---|---|---|
| 2007/0282271 A1* | 12/2007 | Kaplan | A61F 5/445 | 604/174 |
| 2008/0269700 A1* | 10/2008 | O'Toole | A61F 5/445 | 604/332 |
| 2008/0300556 A1* | 12/2008 | Fenton | A61F 5/4404 | 604/339 |
| 2009/0012483 A1* | 1/2009 | Blott | A61M 1/0088 | 604/315 |
| 2009/0163883 A1* | 6/2009 | Christensen | A61F 5/445 | 604/328 |
| 2009/0234312 A1* | 9/2009 | O'Toole | A61F 5/448 | 604/332 |
| 2010/0114044 A1* | 5/2010 | Cramer | A61F 5/443 | 604/332 |
| 2010/0168693 A1* | 7/2010 | Edvardsen | A61F 5/451 | 604/355 |
| 2010/0324511 A1* | 12/2010 | Dove | A61F 5/445 | 604/342 |
| 2011/0213322 A1* | 9/2011 | Cramer | A61F 5/443 | 604/344 |
| 2013/0035653 A1* | 2/2013 | Kannankeril | A61F 5/445 | 604/333 |
| 2013/0072886 A1* | 3/2013 | Schertiger | A61F 5/445 | 604/333 |
| 2014/0039430 A1* | 2/2014 | Richmann | A61F 5/443 | 604/344 |
| 2014/0309604 A1* | 10/2014 | Paratore | A61F 5/445 | 604/332 |
| 2015/0018788 A1* | 1/2015 | Pham | B32B 7/02 | 604/333 |
| 2015/0018789 A1* | 1/2015 | Ben-Arie | A61F 5/442 | 604/334 |
| 2015/0190198 A1* | 7/2015 | Debel | A61B 50/37 | 604/344 |
| 2015/0209172 A1* | 7/2015 | Richmann | A61F 5/445 | 604/332 |
| 2015/0320585 A1* | 11/2015 | Fattman | A61F 5/4407 | 604/344 |

* cited by examiner

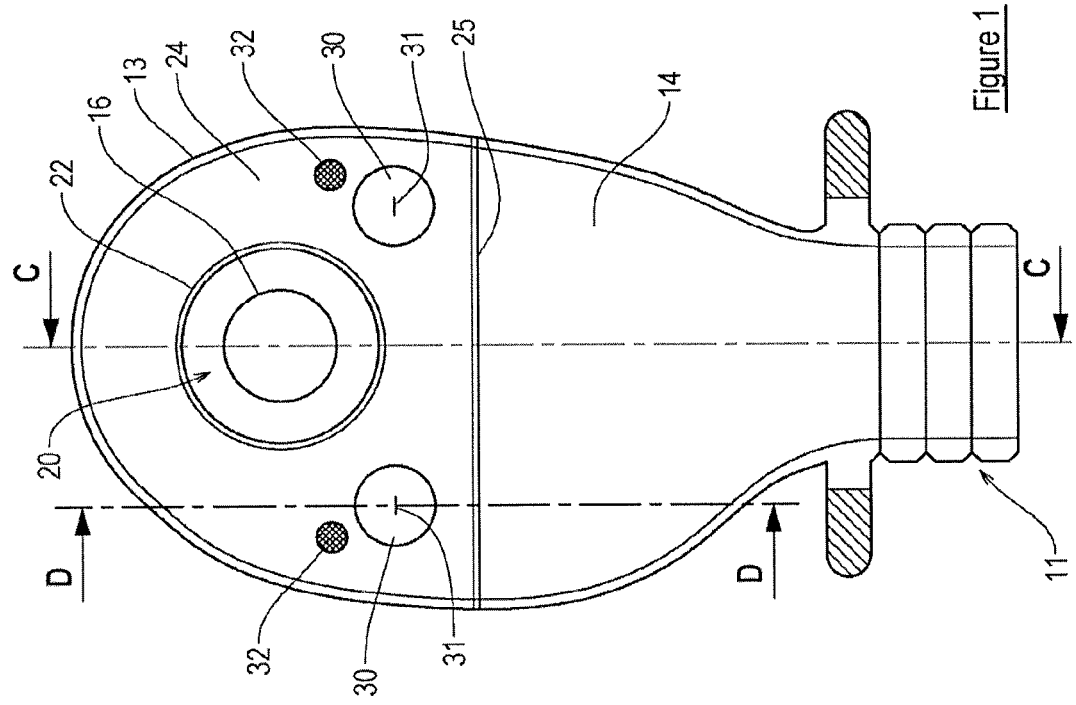
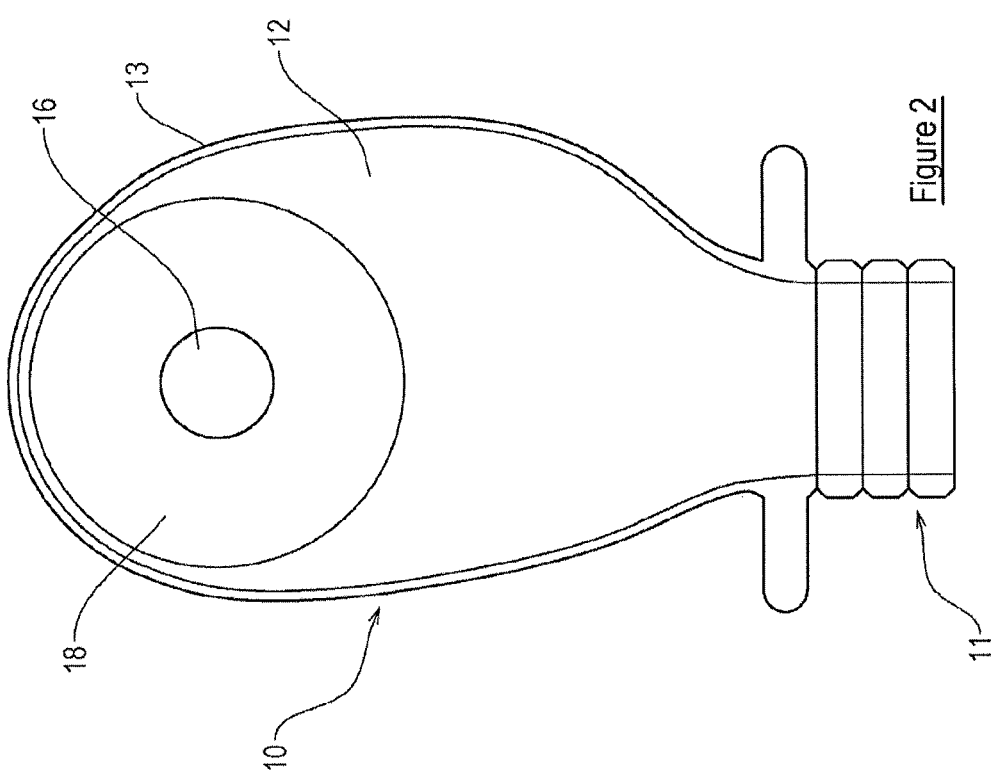

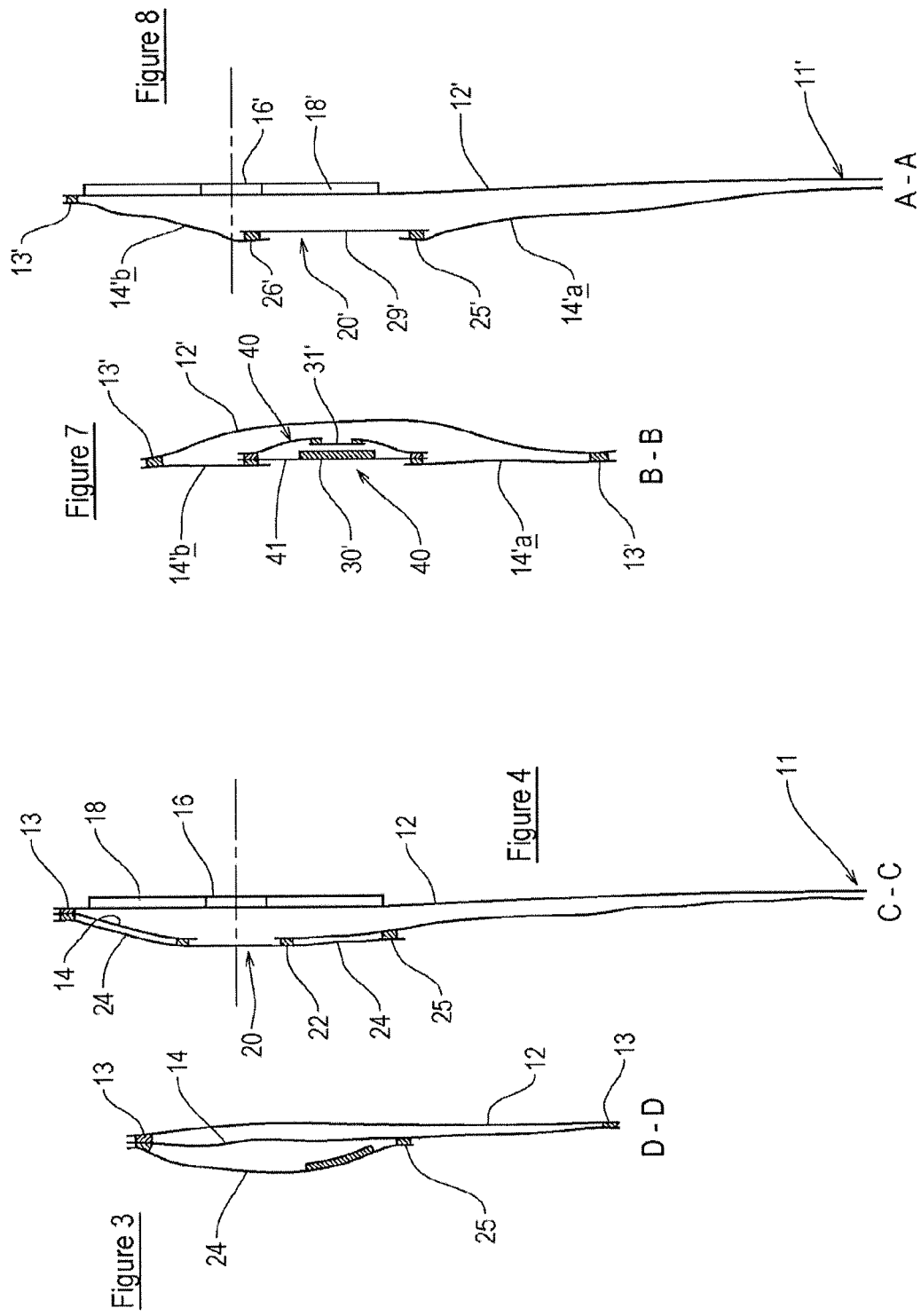

OSTOMY APPLIANCE

SUMMARY OF THE INVENTION

The invention relates to an ostomy appliance for collecting human waste. It should be understood that the invention can be utilised in drainable and non-drainable ostomy appliances. The invention is applicable to both one piece and two piece ostomy appliances.

According to a first aspect of the invention, we provide an ostomy appliance having:

first and second walls connected to each other at or near their peripheries, the first wall having a stoma-receiving opening; and a waste collecting cavity defined between the first and second walls, wherein the second wall includes viewing portion through which the stoma-receiving opening can be viewed.

Further features of the first aspect of the invention are set out in claims 2 to 26 appended hereto.

BRIEF DESCRIPTION OF THE DRAWINGS

Embodiments of the invention will now be described by way of example only with reference to the accompanying drawings, of which:

FIG. 1 is a rear view of a first embodiment of an ostomy appliance in accordance with the present invention;

FIG. 2 is a front view of a first embodiment of an ostomy appliance in accordance with the present invention;

FIG. 3 is a cross-sectional view through the plane D-D of FIG. 1;

FIG. 4 is a cross-sectional view through the plane C-C of FIG. 1;

FIG. 7 is a cross-sectional view through the plane B-B of FIG. 5;

FIG. 8 is a cross-sectional view through the plane A-A of FIG. 5;

DETAILED DESCRIPTION OF THE INVENTION

Figure 5:
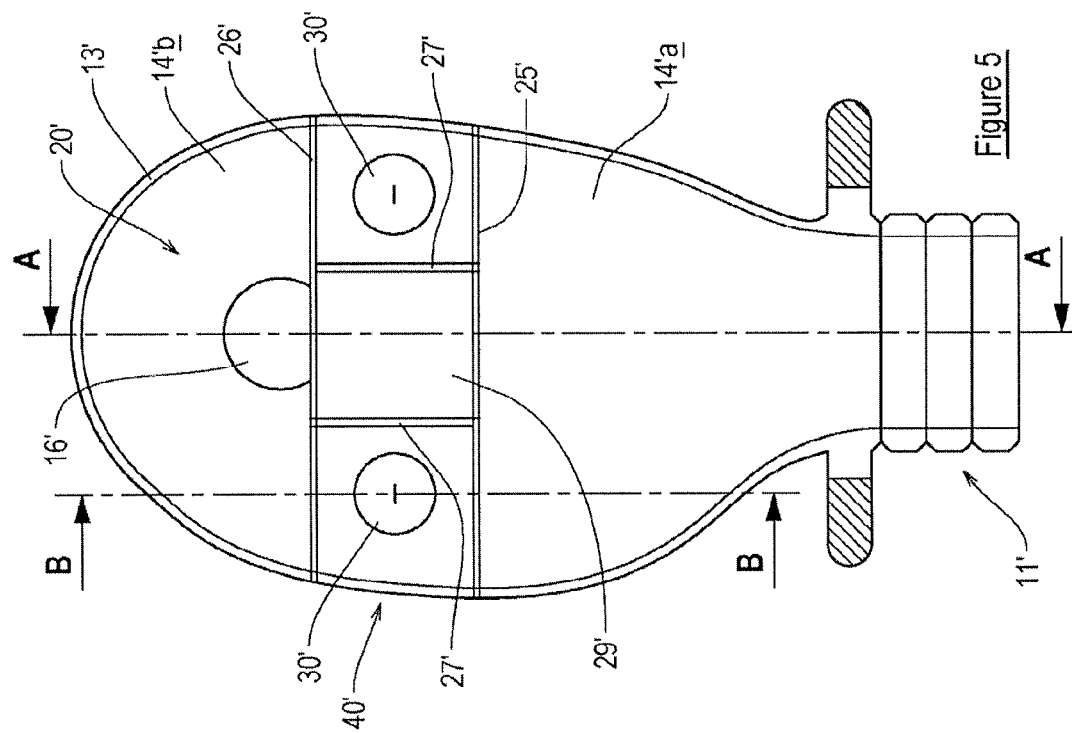
FIG. 5 is a rear view of a second embodiment of an ostomy appliance in accordance with the present invention.
Figure 6:
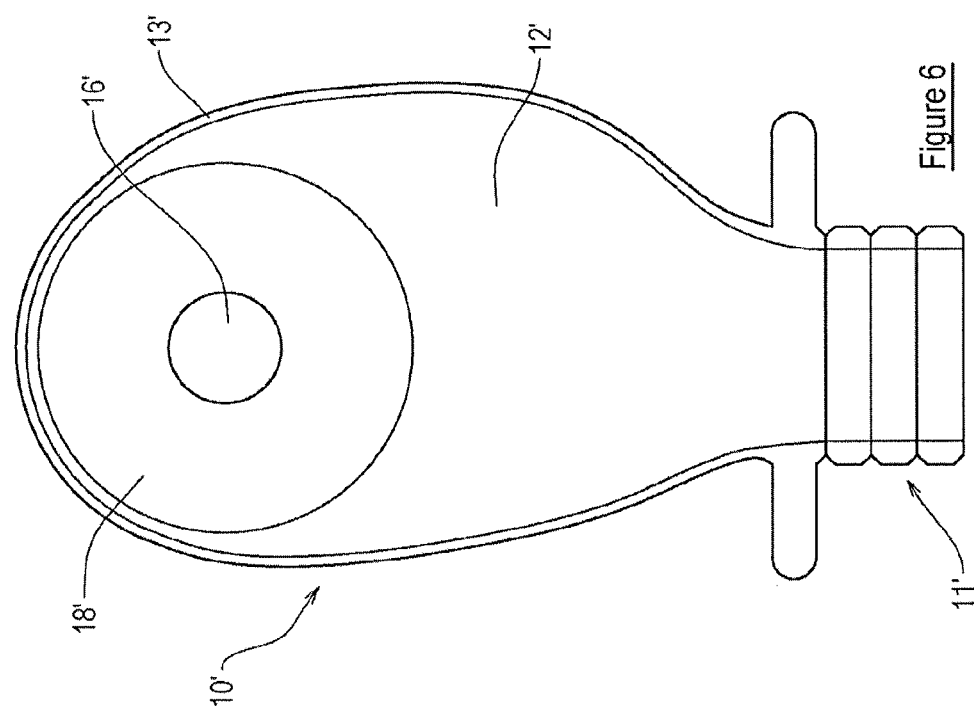
FIG. 6 is a front view of a second embodiment of an ostomy appliance in accordance with the present invention.
Figure 9:
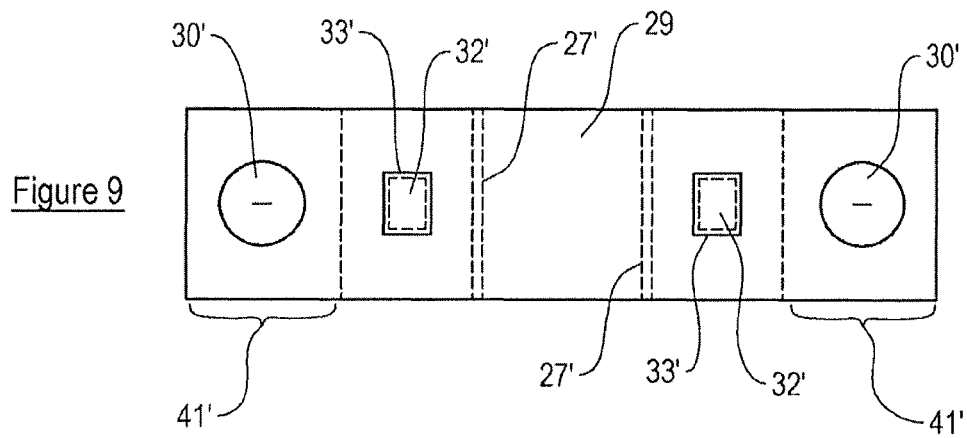
FIG. 9 is a plan view of a component part of the second embodiment of the present invention.

Referring firstly to FIGS. 1, 2, 3 and 4, these show a first embodiment of an ostomy appliance in accordance with the present invention, shown generally at 10. The general construction of the ostomy appliance 10 is similar to those well known in the art and in that sense it includes first 12 and second 14 walls connected to each other at or near their peripheries, for example by heat welding or using an adhesive. The walls 12, 14 are opaque other than where indicated below. The ostomy appliance shown is a drainable appliance, meaning that its contents can be emptied through an opening 11 between the walls 12, 14.

The first wall 12 has a stoma-receiving opening 16 and is connected to a generally circular flange 18 which is manufactured from the hydrocolloid material, for adhering the appliance 10 to a user around their stoma. The first 12 and second 14 walls define a waste collecting cavity (seen more clearly in FIG. 4).

The ostomy appliance 10 in accordance with the present invention advantageously includes a viewing portion 20 in the second wall 14 thereof through which the stoma receiving opening 16, and thus the stoma, can be viewed by a user. In this embodiment the viewing portion 20 is generally circular although it should be appreciated that it could take many other forms so long as it is possible for the user to view at least a significant portion of the stoma-receiving opening 16.

In the present invention the viewing portion is a transparent portion of an upper part of the second wall 14 generally opposite the stoma receiving opening 16. In more detail, as can be seen from FIGS. 1, 3 and 4, the second wall 14 includes, in an upper region thereof, an aperture 22 which defines the viewing portion 20 through which the stoma-receiving opening can be seen. The aperture 22 is closed by a transparent additional wall 24 which is connected to an exterior surface of the second wall 14 at or near its peripheries 13, by a linear connection region 25, and around the aperture 22 (e.g. further heat welds or adhesives).

As best seen in FIG. 1 the appliance 10 includes two filters 30 which permit gas to escape from the space between the walls 14, 24 to atmosphere. Each gas filter 30 is positioned on an internally facing surface of the wall 24 and is adhered thereto adjacent an aperture (e.g. a slit) 31 in the wall 24. As can be seen from FIG. 1 the appliance 10 also includes a pair of gas flow path openings 32 each of which is positioned in the upper region (i.e. that which is covered by the wall 24) of the wall 14 and serves to provide a gas flow path between the main waste collecting cavity (between walls 12, 14) and the cavity between the walls 14 and 24.

Now referring to FIGS. 5 to 8 these show a second embodiment of an ostomy appliance 10' in accordance with the present invention. Feature similar to those in the first embodiment have been given the same reference numeral with the addition of a prime (') symbol and this will not be described in any further detail with regard to this embodiment.

This embodiment differs from the first embodiment in the arrangement and construction of the viewing portion 20' and the gas filters 30'. Rather than the viewing portion 20' being a circular portion, in this embodiment it is an upper portion 14'b of the second wall 14'. This D-shaped portion 14'b of the wall 14' is transparent and thus it is possible for the user to view the stoma-receiving opening 16'. The remainder of the wall 14' is opaque as is the entire wall 12'.

In the ostomy appliance 10' the gas filters 30' are provided as part of a gas filter assembly 40' which in the present example forms an integral part of the second wall 14'. In other words the gas filter assembly 40' is connected to and positioned in between the upper 14'b and lower 14'a portions of the second wall 14'. The gas filter assembly 40' is therefore connected to the viewing portion 20'.

The gas filter assembly 40' defines, in the present example, two gas filter chambers, each chamber containing one gas filter 30'. It should be appreciated, however, that fewer or more gas filter chambers could be provided and the number of gas filters within each chamber can be more than one. In the present example, as will become apparent hereinafter, the gas filter chambers are spaced from each other by a portion of wall 29'.

Figure 10:
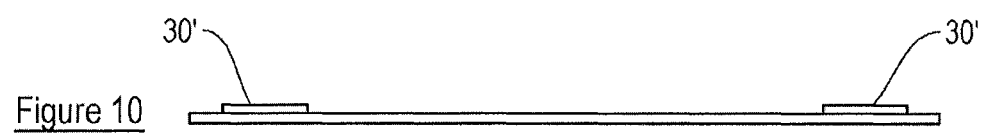
FIGS. 10 to 12 are side views of the component part of FIG. 9 is progressive stages of manufacture.
Figure 11:
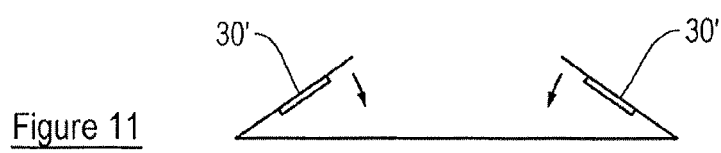
Figure 12:

Turning to FIGS. 9 through 12, these show the gas filter assembly 40' in plan view (FIG. 9) and then in its progressive stages of manufacture (FIGS. 10 through 12). As can be seen from FIG. 9 the gas assembly 40' is a strip/sheet of material (identical or similar to the material used for the walls of the appliance 10'—it must be liquid and gas impermeable) and is generally rectangular. Each gas chamber is defined by a folded end portion 41' of the sheet. Positioned either side of the central wall portion 29' is a portion of the sheet onto which the folded portion 41' is folded. This portion of the sheet includes a gas flow path 32' which in this example is covered by a gas permeable membrane 33'. As can be seen from FIGS. 11 and 12 remote portions 41' of the sheet are folded back towards the central wall portion 29' where they are then adhered to the remainder of the sheet at linear connection zones 27'. As seen in FIG. 12 this provides a gas filter assembly 40' including a pair of gas filter chambers which are spaced from each other by the wall portion 29'. This component part is then connected to the upper transparent portion 14'*b* of the second wall 14' at lateral weld line 26' and to the lower portion 14'A of the wall 14' at the linear lateral weld line 26'. The gas filter assembly 40' thus becomes an integral part of the second wall 14' whilst permitting waste gases to exit from the main cavity (between the walls 12', 14'), through the gas chambers and to atmosphere.

It will be appreciated that any of the features of the second embodiment can be incorporated into the first embodiment, and vice versa, without departing with the scope of the present invention.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. An ostomy appliance having:
   first and second walls connected to each other at or near their peripheries, the first wall having a stoma-receiving opening; and
   a waste collecting cavity defined between the first and second walls,
   wherein the second wall comprises an upper wall and a lower wall, wherein the entire upper wall is disposed opposite the stoma-receiving opening and is transparent to provide a viewing portion through which the stoma-receiving opening can be viewed and the entire lower wall is opaque, and wherein the upper wall and lower wall are separate flexible liquid and gas impermeable sheets;
   wherein the upper wall includes a lower edge; and
   wherein the lower wall includes an upper edge and a remainder of a lower wall;
   wherein the lower edge of the upper wall is connected to the upper edge of the lower wall by a substantially linear connection region; and
   wherein the remainder of the lower wall is positioned entirely below the upper wall.

2. The ostomy appliance of claim 1 wherein the appliance includes an outlet positioned at a bottom thereof for permitting emptying of the waste collecting cavity, and wherein a portion of the second wall positioned adjacent the outlet is opaque.

3. The ostomy appliance of claim 1 wherein the appliance includes a further wall connected to the first and second walls at or near their peripheries, the further wall including an opening or a transparent portion which is substantially aligned with the viewing portion of the upper wall.

4. The ostomy appliance of claim 1 wherein the appliance includes an intermediate wall positioned in between the first and second walls which includes an opening or a transparent portion which is substantially aligned with the viewing portion of the second wall.

5. The ostomy appliance of claim 4 wherein the intermediate wall is connected to the second wall at a connection zone.

6. The ostomy appliance of claim 5 wherein said connection zone is positioned around the viewing portion of the second wall.

7. The ostomy appliance of claim 6 wherein said connection zone extends completely around the viewing portion of the second wall.

8. The ostomy appliance of claim 7 wherein the first and intermediate walls are substantially the same length and wherein the second wall is shorter in length than the first and intermediate walls.

9. The ostomy appliance of claim 1 wherein the appliance includes a further viewing portion through which a lower portion of the waste collecting cavity can be viewed.

10. The ostomy appliance of claim 9 wherein the appliance includes two or more viewing portions through which the stoma-receiving opening can be viewed.

11. The ostomy appliance of claim 1 wherein a gas flow path is provided from the waste collecting cavity though the second wall, and if present, an intermediate wall, to atmosphere.

12. The ostomy appliance of claim 11 wherein the gas flow path includes one or more gas vents in the wall(s) of the appliance.

13. The ostomy appliance according to claim 12 wherein each of the one or more gas vents includes or is covered by a filter.

14. The ostomy appliance of claim 1 wherein the appliance includes a gas filter assembly supporting one or more gas filters, wherein the assembly includes a pair of walls which are connected to each other, and wherein the gas filter assembly is connected to the viewing portion of the second wall.

15. The ostomy appliance of claim 14 wherein the gas filter assembly forms an integral part of the second wall.

16. The ostomy appliance of claim 15 wherein the gas filter assembly defines two gas filter chambers, each chamber containing at least one gas filter.

17. The ostomy appliance of claim 16 wherein the gas filter chambers are spaced from each other.

18. The ostomy appliance of claim 17 wherein the gas filter assembly is manufactured from a single sheet of material, with each gas chamber being defined by a folded portion of the sheet.

19. The ostomy appliance of claim 18 wherein each folded portion is folded towards a central region of the assembly.

20. The ostomy appliance of claim 19 wherein a remote edge of each folded portion is connected to a remainder of the sheet to form the gas filter chamber.

21. The ostomy appliance of claim 20 wherein the remote edge is heat welded in place.

22. An ostomy appliance having:
   first and second walls connected to each other at or near their peripheries, the first wall having a stoma-receiving opening; and
   a waste collecting cavity defined between the first and second walls, wherein the second wall comprises an upper wall and a lower wall, wherein the entire upper wall is disposed opposite the stoma-receiving opening and is transparent to provide a viewing portion through which the stoma-receiving opening can be viewed and the entire lower wall is opaque, and wherein the upper wall and lower wall are separate flexible liquid and gas impermeable sheets and a lower edge of the upper wall is connected to an upper edge of the lower wall by a substantially linear weld.

* * * * *